US010722474B2

(12) United States Patent
Bell

(10) Patent No.: US 10,722,474 B2
(45) Date of Patent: Jul. 28, 2020

(54) EDDS CHELATED NANOCERIA WITH CATALASE-LIKE ACTIVITY

(71) Applicant: Cerion, LLC, Rochester, NY (US)

(72) Inventor: Eric Leslie Bell, Webster, NY (US)

(73) Assignee: Cerion, LLC, Rochester, NY (US)

( * ) Notice: Subject to any disclaimer, the term of this patent is extended or adjusted under 35 U.S.C. 154(b) by 0 days.

(21) Appl. No.: 15/545,065

(22) PCT Filed: Jan. 20, 2016

(86) PCT No.: PCT/US2016/014076

§ 371 (c)(1), (2) Date: Jul. 20, 2017

(87) PCT Pub. No.: WO2016/118592

PCT Pub. Date: Jul. 28, 2016

(65) Prior Publication Data

US 2018/0325832 A1 Nov. 15, 2018

Related U.S. Application Data

(60) Provisional application No. 62/125,381, filed on Jan. 20, 2015.

(51) Int. Cl.

| | |
|---|---|
| ***A61K 9/14*** | (2006.01) |
| ***A61K 9/51*** | (2006.01) |
| ***A61K 9/10*** | (2006.01) |
| ***A61K 33/24*** | (2019.01) |
| ***A61K 31/197*** | (2006.01) |
| ***A61K 47/18*** | (2017.01) |
| ***A61K 47/12*** | (2006.01) |
| ***A61K 9/16*** | (2006.01) |
| ***F41C 33/00*** | (2006.01) |
| ***F41C 33/04*** | (2006.01) |
| *A61K 9/00* | (2006.01) |
| *F41C 33/02* | (2006.01) |

(52) U.S. Cl.

CPC .............. *A61K 9/5123* (2013.01); *A61K 9/10* (2013.01); *A61K 9/14* (2013.01); *A61K 9/1688* (2013.01); *A61K 9/5192* (2013.01); *A61K 31/197* (2013.01); *A61K 33/24* (2013.01); *A61K 47/12* (2013.01); *A61K 47/183* (2013.01); *F41C 33/008* (2013.01); *F41C 33/048* (2013.01); *A45F 2200/0591* (2013.01); *A61K 9/0019* (2013.01); *F41C 33/0245* (2013.01); *F41C 33/041* (2013.01)

(58) Field of Classification Search

None

See application file for complete search history.

(56) References Cited

U.S. PATENT DOCUMENTS

| | | | |
|---|---|---|---|
| 5,525,249 | A | 6/1996 | Kordonsky et al. |
| 6,955,589 | B2 | 10/2005 | Kordonski et al. |
| 7,534,453 | B1 | 5/2009 | Rzigalinski et al. |
| 8,357,311 | B2 | 1/2013 | Shirota |
| 8,679,344 | B2 | 3/2014 | Allston et al. |
| 9,034,392 | B2 | 5/2015 | Reed et al. |
| 2013/0337083 | A1 | 12/2013 | Reed et al. |
| 2014/0032333 | A1 | 1/2014 | Hemann |

FOREIGN PATENT DOCUMENTS

| | | | |
|---|---|---|---|
| CN | 101568615 | A | 10/2009 |
| JP | 2006328442 | A | 12/2006 |
| JP | 2010502559 | A | 1/2010 |
| WO | 2005035560 | A1 | 4/2005 |
| WO | 2007002662 | A2 | 1/2007 |
| WO | 2008030805 | | 3/2008 |
| WO | 2008030815 | A2 | 3/2008 |

OTHER PUBLICATIONS

Knepper, T. Synthetic chelating agents and compounds exhibiting complexing properties in the aquatic environment. Trends in Analytical Chemistry, vol. 22, No. 10, 2003, pp. 708-724.*

International Search Report and Written Opinion for International Application No. PCT/US2016/014076, dated Apr. 20, 2016—10 Pages.

Masui et al., "Synthesis of Cerium Oxide Nanoparticles by Hydrothermal Crystallization with Citric Acid", J. Mater. Sci. Lett., 2002, vol. 21, pp. 489-491.

Rzigalinski, B., "Nanoparticles and Cell Longevity", Technology in Cancer Research and Treatment , 2005 vol. 4, No. 6, pp. 651-659.

Chinese Office Action for Chinese Application No. 2016800112555, dated Jan. 9, 2020 with translation, 22 pages.

Partial Translation of the Japan Tappi Journal. (2000), pp. 184-197, vol. 54, No. 2.

Notice of Reasons for Rejection for Japanese Application No. 2017-556792, dated Nov. 12, 2019, with translation, 9 pages.

* cited by examiner

*Primary Examiner* — Jessica Worsham

(74) *Attorney, Agent, or Firm* — RatnerPrestia

(57) ABSTRACT

A process for making nanoparticles of biocompatible materials is described, wherein an aqueous reaction mixture comprising cerous ion, ethylenediaminedisuccinic acid, an oxidant, water, and optionally citric acid, is provided along with temperature conditions to directly form within the reaction mixture, a stable dispersion of cerium oxide nanoparticles. Biocompatible, nanoparticles comprised of cerium oxide, ethylenediaminedisuccinic acid, and optionally citric acid, are described. An increase in catalase-like enzyme activity is demonstrated by cerium oxide nanoparticles prepared with citric acid and ethylenediaminedisuccinic acid.

6 Claims, No Drawings

EDDS CHELATED NANOCERIA WITH CATALASE-LIKE ACTIVITY

CROSS-REFERENCE TO RELATED APPLICATIONS

This application is a U.S. National Phase application of PCT International Application No. PCT/US16/014076, filed Jan. 20, 2016, which claims priority to U.S. Provisional Patent Application Ser. No. 62/125,381, EDDS CHELATED NANOCERIA WITH CATALASE-LIKE ACTIVITY, filed Jan. 20, 2015, the disclosures of which are incorporated herein by reference in their entirety.

FIELD OF THE INVENTION

The present invention relates in general to improvements in the fields of nanoscience and nanomedicine. In particular, the invention relates to methods of preparing nanoparticles, to nanoparticles comprising biocompatible materials, and to nanoparticles with catalase-like activity. The invention also relates the use of such nanoparticles to catalyze the elimination of hydrogen peroxide, or to prevent or to treat disease, more particularly, to reduce the effects of oxidative stress due to hydrogen peroxide, such as, by administration of nanoparticles with catalase-like activity.

BACKGROUND OF THE INVENTION

Oxidative stress plays a major role in the pathogenesis of many human diseases, and in particular, neurodegenerative diseases. Treatment with antioxidants, which may reduce particular free radical species, therefore, may prevent tissue damage and improve both survival and neurological outcome. Hydrogen peroxide is a by-product of many important cellular processes; however, it is also a known generator or precursor of free radicals in physiological environments. Catalase is a naturally occurring antioxidant enzyme (redox protein) that prevents excessive buildup of hydrogen peroxide by catalyzing the breakdown of hydrogen peroxide into water and oxygen. Antioxidant drugs with activity that mimics the cellular enzyme catalase (i.e. catalase-like activity) may slow the progression of various oxidative stress related diseases and events, such as ischemic stroke.

The origin of the use of nanoceria in nanomedicine can be traced to the seminal work of Bailey and Rzigalinski, wherein the application of ultrafine cerium oxide particles to brain cells in culture was observed to greatly enhanced cell survivability, as described by Rzigalinski in Nanoparticles and Cell Longevity, Technology in Cancer Research & Treatment 4(6), 651-659 (2005). More particularly, rat brain cell cultures in vitro were shown to survive approximately 3-4 times longer when treated with 2-10 nanometer (nm) sized cerium oxide nanoparticles synthesized by a reverse micelle micro emulsion technique, as disclosed by Rzigalinski et al. in U.S. Pat. No. 7,534,453, filed Sep. 4, 2003.

Subsequently, a host of problems with these particular nanoceria particles was disclosed by Rzigalinski et al. in WO 2007/002662. Nanoceria produced by the reverse micelle micro emulsion technique suffered as follows: (1) particle size was not well-controlled within the reported 2-10 nanometer (nm) range, making variability between batches high; (2) tailing of surfactants, such as sodium bis(ethylhexyl)sulphosuccinate, also known as docusate sodium or (AOT), used in the reverse micelle synthetic process into the final product caused toxic responses; (3) inability to control the amount of surfactant tailing posed problems with agglomeration when these nanoparticles were placed in biological media, resulting in reduced efficacy and deliverability; and (4) instability of the valence state of cerium (+3/+4) over time. Thus, the cerium oxide nanoparticles produced by the reverse micelle micro emulsion technique were highly variable from batch to batch, and showed higher than desired toxicity to mammalian cells.

As an alternative, Rzigalinski et al. in WO 2007/002662 describe the biological efficacy of nanoceria synthesized by high temperature techniques, obtained from at least three commercial sources. These alternative sources of cerium oxide nanoparticles were reported to provide superior reproducibility of activity from batch to batch. It was further reported that, regardless of source, cerium oxide particles having a small size, narrow size distribution, and low agglomeration rate are most advantageous.

These inventors (Rzigalinski et al.) also report therein that for delivery, the nanoparticles were advantageously in a non-agglomerated form. To accomplish this, they reported that stock solutions of about 10% by weight of nanoceria could be sonicated in ultra-high purity water or in normal saline prepared with ultra-high purity water. However, we have confirmed what others have observed, that sonicated aqueous dispersions of nanoceria (synthesized by high temperature techniques and obtained from commercial sources) are highly unstable, and settle rapidly (i.e. within minutes), causing substantial variability in administering aqueous dispersions of nanoceria derived from these sources. We have also observed that administration of these sonicated aqueous dispersions of nanoceria (e.g. obtained from Sigma-Aldrich) to mice result is rapid deposition of ceria in the liver and kidneys along with rapid decline in the health of the animals.

While cerium oxide containing nanoparticles can be prepared by a variety of techniques known in the art, the particles typically require a stabilizer to prevent undesirable agglomeration. In regard to biocompatible nanoceria stabilizers used previously, Masui et al., J. Mater. Sci. Lett. 21, 489-491 (2002) describe a two-step hydrothermal process that directly produces stable aqueous dispersions of ceria nanoparticles that use citrate buffer as a stabilizer. However, this process is both time and equipment intensive, requiring two separate 24 hours reaction steps in closed reactors.

DiFrancesco et al. in PCT/US2007/077545, METHOD OF PREPARING CERIUM DIOXIDE NANOPARTICLES, filed Sep. 4, 2007, describes the oxidation of cerous ion by hydrogen peroxide under highly acidic conditions ($pH<4.5$) in the presence of biocompatible $\alpha$-hydroxy carboxylic acid stabilizers, such as lactic acid, tartaric acid, gluconic acid and 2-hydroxybutanoic acid. Specifically, the stabilizer lactic acid and the stabilizer combination of lactic acid and ethylenediaminetetraacetic acid (EDTA) are shown in working examples to directly produce stable dispersions of nanoceria particles of average particle size in the range of 3-8 nm under highly acidic reaction conditions.

Commonly assigned U.S. Pat. No. 9,034,392 describes the oxidation of cerous ion by hydrogen peroxide in the presence of citric acid (CA) and ethylediaminetetraacetic acid (EDTA), wherein the molar ratio of CA to EDTA ranges from about 0.1 to about 3.0, whereby aqueous dispersions of stabilized cerium oxide nanoparticles are formed directly in the reaction mixture, without isolation of the nanoparticles. Cerium oxide nanoparticles stabilized with a combination of CA and EDTA in this range of molar amounts are shown to synergistically reduce cell death due to oxidative stress in an ex vivo murine brain slice model of ischemic stroke.

Commonly assigned US Patent Application 2014/0322333 describes the oxidation of cerous ion by hydrogen peroxide in the presence of citric acid and a chelant selected from the group consisting of nitrilotriacetic acid (NTA), ethylene glycol tetraacetic acid (EGTA) and diethylenetriaminepentaacetic acid (DTPA), whereby aqueous dispersions of stabilized cerium oxide nanoparticles are formed directly in the reaction mixture, without isolation of the nanoparticles. These stabilized cerium oxide nanoparticles are shown to reduce cell death due to oxidative stress in an ex vivo murine brain slice model of ischemic stroke.

As described above, various methods have been reported for preparing aqueous dispersions of biocompatibly stabilized cerium oxide nanoparticles. Antioxidant drugs with increased catalase-like activity will more quickly reduce the tissue damage resulting from an excess buildup of hydrogen peroxide, and/or may enable a corresponding reduction in drug dosage, thereby reducing the drug cost and/or drug side effects to the patient. Thus, there remains a need for increased catalase-like activity in aqueous dispersions of stabilized cerium oxide nanoparticles.

SUMMARY OF THE INVENTION

In accordance with a first aspect of the invention, a process of making a dispersion of nanoparticles is provided, comprising: forming a reaction mixture comprising cerous ion, ethylenediaminedisuccinic acid, an oxidant, water, and optionally further comprising citric acid; optionally, heating or cooling the reaction mixture; and thereby forming in the reaction mixture, without isolation of the nanoparticles, a dispersion of cerium oxide nanoparticles.

In a second aspect of the invention, a cerium oxide nanoparticle prepared in the presence of ethylenediaminedisuccinic acid, and optionally further prepared in the presence of citric acid, is provided.

In a third aspect of the invention, a pharmaceutical composition for the prevention and/or treatment of an oxidative stress related event or disease, and in particular, a central nervous system disease, such as multiple sclerosis or amyotrophic lateral sclerosis, comprises a cerium oxide nanoparticle prepared in the presence of ethylenediaminedisuccinic acid, and optionally further prepared in the presence of citric acid, is provided.

In a fourth aspect of the invention, a process of preventing (i.e. prophylactically treating) an oxidative stress related event or an oxidative stress related disease, and in particular, a central nervous system disease, such as multiple sclerosis or amyotrophic lateral sclerosis, comprising administering prior to the onset of an event or disease, an effective amount of a cerium oxide nanoparticle prepared in the presence of ethylenediaminedisuccinic acid, optionally further prepared in the presence of citric acid; or, a nanoparticle comprising cerium oxide, ethylenediaminedisuccinic acid, and optionally further comprising citric acid, is provided.

In a sixth aspect of the invention, a process of treating an oxidative stress related event, in particular ischemic stroke, or an oxidative stress related disease, and in particular, a central nervous system disease, such as multiple sclerosis or amyotrophic lateral sclerosis, comprising administering after the onset of an event or disease, an effective amount of a cerium oxide nanoparticle prepared in the presence of ethylenediaminedisuccinic acid, and optionally further prepared in the presence of citric acid; or, a nanoparticle comprising cerium oxide, ethylenediaminedisuccinic acid, and optionally further comprising citric acid, is provided.

DETAILED DESCRIPTION OF THE INVENTION

It is to be understood that elements not specifically shown or described may take various forms well known to those skilled in the art. The invention is defined by the claims.

In this application, the term nanoparticle includes particles having a mean diameter of less than 100 nm. For the purposes of this disclosure, unless otherwise stated, the diameter of a nanoparticle refers to its average crystallographic particle diameter, which can be estimated by a peak width analysis of powder X-ray diffraction (XRD) spectra using the Scherrer equation. Alternatively, the geometric particle diameter can be estimated by analysis of transmission electron micrographs (TEM). Alternatively, the hydrodynamic diameter, which includes molecular adsorbates and the accompanying solvation shell of the particle, can be determined by dynamic light scattering techniques. In addition, for substantially monodisperse nanoparticle size distributions having geometric size in the 1-10 nm range, XRD can also reveal a very low angle scattering peak that is a direct measure of size of the scattering centers.

In this application, particles described as "substantially non-agglomerated" have a hydrodynamic diameter less than or equal to twice the crystallite diameter determined by XRD using the Scherrer method.

In this disclosure, the term "metal" in referring to elements of the Periodic Table includes all elements other than those of the following atomic numbers: 1-2, 5-10, 14-18, 33-36, 52-54, 85 and 86.

The term "transition metal" is understood to encompass the 30 chemical elements of atomic number 21 to 30, 39 to 48, 57, and 72 to 80, which are included in Periods 4, 5, 6, respectively, of the Periodic Table.

The term "rare earth metal" is understood to encompass the 14 lanthanide chemical elements of atomic number 58 to 71, and the 14 actinide chemical elements of atomic number 90 to 103.

The term "alkali metal" is understood to encompass the 6 chemical elements forming Group 1 of the Periodic Table, those of atomic number 3, 11, 19, 37, 55, and 87.

The term "alkaline earth metal" is understood to encompass the 6 chemical elements forming Group 2 of the Periodic Table, those of atomic number 4, 12, 20, 38, 56, and 88.

The chemical term "ethylenediaminedisuccinic acid" is alternatively known by chemical names such as ethylenediamine-N,N'-disuccinic acid; N,N'-ethylenediamine disuccinic acid; L-ethylenediaminedisuccinic acid; N,N'-ethylenediaspartic acid; 2-[2-(1,2-dicarboxyethylamino) ethylamino]butanedioic acid (IUPAC name); CAS Number 20846-91-7; molecular formula $C_{10}H_{16}N_2O_8$; and acronyms EDDS and EDSS. There are two chiral centers in the structure of EDDS, giving rise to two enantiomeric isomers: [R,R']-EDDS and [S,S']-EDDS, and one meso isomer [R,S]-EDDS. [S,S']-EDDS has been commercially available under the trade names Enviomet C265 and Natriquest E30, and is known to be biodegradable.

The chemical term "ethylenediaminedisuccinic acid" is also understood to encompass any salts thereof, comprising, for example, the reaction product of ethylenediaminedisuccinic acid with a base, such as, for example, an alkali metal hydroxide, such as, sodium hydroxide or potassium hydroxide. In this manner, one or more of the acidic protons in ethylenediaminedisuccinic acid is/are replaced by another cation, such as, for example, an alkali metal cation or an alkaline earth metal cation. Thus, mono, di, tri and tetra alkali metal salts of ethylenediaminedisuccinate may be formed. For example, an aqueous solution of [S,S']-Ethylenediamine-N,N'-disuccinic acid trisodium salt is commercially available from Sigma-Aldrich (catalog number 92698).

The chemical term “citric acid” is understood to include salts thereof, such as, for example, metal cation salts of citrate anion. In this manner, one or more of the acidic protons in citric acid is/are replaced by another cation, such as, for example, an alkali metal cation or an alkaline earth metal cation.

In this application, the term “crystalline” is understood to describe a material that displays at least one X-ray or electron diffraction peak (excluding very low angle XRD peaks not assignable to a crystal structure), wherein the peak intensity is discernibly greater than the background scattering (baseline noise). The terms “semi-crystalline” or “partially crystalline” are understood to describe a material that displays only broad X-ray or electron diffraction peaks of low peak intensity due to a lack of long-range order. The term “amorphous” is understood to describe a material that does not display any X-ray or electron diffraction peaks (excluding very low angle XRD peaks not assignable to a crystal structure).

In this application, various cerium-containing materials are nominally described as a “ceria” phase, “cerium oxide” phase or “cerium dioxide” phase. It will be understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for bulk oxide phases comprised of metal cations of multiple oxidation states, it is understood that the total amount of oxidic anions present will be determined by the specific amounts of the various oxidation states of the metal cations present, for example, cerous ion ($Ce^{3+}$) and ceric ion ($Ce^{4+}$), such that charge neutrality is maintained. For non-stoichiometric phases nominally described as metal dioxides, this is embodied in the chemical formula $MO_{2-\delta}$wherein the value of δ (delta) may vary.

For a cerium oxide, $CeO_{2-\delta}$, the value of □ (delta) typically ranges from 0.0 to 0.5, the former denoting cerium (IV) oxide, $CeO_2$, the latter denoting cerium (III) oxide, $CeO_{1.5}$ (alternatively denoted $Ce_2O_3$). While not wishing to be held to any particular theory, the value of δ (delta) may be interpreted as the amount of oxygen vacancies present relative to cerium (IV) oxide ($CeO_2$). For each oxygen di-anion vacancy present, two cerous ions ($Ce^{3+}$) are present, to preserve charge neutrality.

In this application, the term “cerium dioxide” is understood to describe Cerium (IV) oxide ($CeO_2$).

In this application, the term “ceria” is understood to describe a cerium oxide comprising ceric ion (i.e. $Ce^{4+}$ or cerium (IV) ion), encompassing a range of non-stoichiometric materials described by the chemical formula, $CeO_{2-\delta}$, wherein the value of □ (delta) ranges from 0.0 to less than 0.5.

In this application, the terms “nanoceria particles” and “ceria nanoparticles” have the same meaning and are used interchangeably.

In accordance with one aspect of the invention, a process is provided comprising: forming a reaction mixture comprising cerous ion, ethylenediaminedisuccinic acid, an oxidant, and water; and thereafter forming in the reaction mixture a dispersion of ceria nanoparticles.

In accordance with another aspect of the invention, a process is provided comprising: forming a reaction mixture comprising cerous ion, citric acid, ethylenediaminedisuccinic acid, an oxidant, and water; and thereafter forming in the reaction mixture a dispersion of ceria nanoparticles In a particular embodiment, the dispersion of nanoparticles is formed directly in the reaction mixture, without isolation of the nanoparticles.

In particular embodiments, the reaction mixture is heated or cooled to a temperature in the range of about 0° C. to about 100° C. In particular embodiments, the reaction mixture is heated or cooled to temperatures greater than 20° C., or less than or equal to 20° C. In various embodiments, the reaction mixture is heated or cooled to temperatures greater than about 30° C., about 40° C., about 50° C., about 60° C., about 70° C., about 80° C. or about 90° C.

In embodiments employing elevated reaction temperatures, the duration of time at elevated temperature may vary widely, for example, from minutes to hours. In particular embodiments, a reaction temperature in the range of about 40° C. to about 100° C. is maintained for a time ranging from about 10 minutes to about 4 hours.

In particular embodiments, the nanoparticles formed are dehydrated, dehydroxylated or deprotonated by heating of the reaction mixture.

In a particular embodiment, the crystallinity of the nanoparticles formed is enhanced by heating of the reaction mixture.

In various embodiments, the source of cerous ion in the reaction mixture is a water soluble salt of cerous ion, such as, for example, cerous nitrate, cerous acetate, or a hydrated salt thereof.

In various embodiments, the reaction mixture or nanoparticles formed comprise a minor amount of a metal ion other than a cerium ion, such as, for example, a transition metal ion, rare earth metal ion other than cerium, alkaline earth metal ion or an alkali metal ion. In particular embodiments, the metal ion other than a cerium ion is an iron ion, such as a ferrous ion or a ferric ion. In other particular embodiments, the metal ion is a platinum, palladium, nickel or copper ion.

In various embodiments, the oxidant includes compounds more oxidizing than molecular oxygen (or an ambient atmosphere of air). In particular embodiments, the oxidant has an aqueous half-cell reduction potential greater than −0.13 volts relative to the standard hydrogen electrode. In particular embodiments the oxidant is an alkali metal or ammonium perchlorate, chlorate, hypochlorite or persulfate; ozone, a peroxide, such as, for example, hydrogen peroxide ($H_2O_2$) or tert-butyl hydroperoxide; or a combination thereof.

In various embodiments, the amount of oxidant employed varies widely in relation to the total amount of oxidizable metal ions present. In particular embodiments the molar amount of oxidant present is equal to or greater than the total molar amount of oxidizable metal ions. In specific embodiments, two-electron oxidants, such as hydrogen peroxide, are present in at least one-half the molar concentration of total oxidizable metal ions, such as cerous ion or ferrous ion.

In various embodiments, the oxidant is added to the reaction mixture alone or concurrently with one or more of the other reactants.

In a particular embodiment, molecular oxygen is passed through the reaction mixture.

In various embodiments, the pH of the reaction mixture is adjusted by the addition of an acid or base to a value greater than 4.5, greater than 5.0, greater 6.0, greater than 7.0, greater than 8.0, greater than 9.0 or greater than 10.0, or greater than 11.0.

In various embodiments, the nanoparticles are used to treat biological tissues or biological media, and are adjusted to physiological pH conditions ranging from about 6.5 to about 8.0, or from about 7.0 to about 7.4.

In particular embodiments, the reaction mixture is adjusted to a pH within suitable physiological conditions. In other embodiments, the final product dispersion of ceria nanoparticles is adjusted to a pH within suitable physiological conditions.

In various embodiments, the reaction mixture is formed in a batch reactor, a continuous reactor or a colloid mill. In particular embodiments of a continuous reactor, a continuous-stirred-tank reactor or a plug-flow reactor are used.

The particular embodiments, various mixing devices known in the art are employed to stir, mix, shear or agitate the contents of the reaction mixture. In various embodiments, mixers comprising stir bars, marine blade propellers, pitch blade turbines or flat blade turbines are used. In particular embodiments, a colloid mill or a Silverson® High Shear Mixer is employed. In a particular embodiment, a high shear mixer that forces the reaction mixture to pass through a screen, wherein holes vary in size from fractions of a millimeter to several millimeters, is employed. In particular embodiments, one or more of the reactants is introduced below the surface of the aqueous reaction mixture. In a particular embodiment, a reactant is introduced below the surface of the aqueous reaction mixture in close proximity to a mixing device.

In various embodiments, the nanoparticles formed are amorphous, semi-crystalline or crystalline. Crystalline nanoparticles may be alternatively described as single particle crystallites or as individual crystallites. In particular embodiments, the nanoparticles formed are characterized by a cerium oxide crystal structure. In a particular embodiment the nanoparticles formed are characterized by a cubic fluorite crystal structure.

In various embodiments, the nanoparticles formed have a hydrodynamic diameter less than 100 nm, less than 80 nm, less than 60 nm, less than 40 nm, less than 20 nm, less than 10 nm, less than 5.0 nm or less than about 2.0 nm.

In a particular embodiment of the invention, a nanoparticle comprising cerium and ethylenediaminedisuccinic acid is provided.

In a particular embodiment of the invention, a nanoparticle comprising cerium, citric acid and ethylenediaminedisuccinic acid is provided.

In a particular embodiment, a nanoparticle comprising ceric ion and ethylenediaminedisuccinic acid is provided.

In a particular embodiment, a nanoparticle comprising ceric ion, citric acid and ethylenediaminedisuccinic acid is provided.

In a particular embodiment, a nanoparticle comprising ceria and ethylenediaminedisuccinic acid is provided.

In a particular embodiment, a nanoparticle comprising ceria, citric acid and ethylenediaminedisuccinic acid is provided.

In a particular embodiment, a nanoparticle comprising ethylenediaminedisuccinic acid and a cerium oxide, cerium hydroxide or cerium oxyhydroxide, is provided.

In a particular embodiment, a nanoparticle comprising citric acid, ethylenediaminedisuccinic acid and a cerium oxide, cerium hydroxide or cerium oxyhydroxide, is provided.

In various embodiments, the zeta potential of the nanoparticle is altered by adjusting the pH, the citric acid content, the ethylenediaminedisuccinic acid content, or a combination thereof; of the nanoparticle dispersion.

In a particular embodiment, the nanoparticle dispersion formed is washed to remove excess ions or by-product salts. In various embodiments, the nanoparticle dispersion is washed such that the ionic conductivity is reduced to less than about 15 millisiemens per centimeter (mS/cm), less than about 10 mS/cm, less than about 5 mS/cm or less than about 3 mS/cm. In particular embodiments, the nanoparticle dispersion formed is washed without isolation of the nanoparticles, such as, for example, by dialysis or diafiltration, whereby a stable nanoparticle dispersion is maintained.

In particular embodiments, the nanoparticle dispersions formed are concentrated to remove excess solvent or excess water. In particular embodiments, the nanoparticle dispersion is concentrated by diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In particular embodiments, the size distribution of the nanoparticles is substantially monomodal. In various embodiments, the nanoparticle size distribution has a coefficient of variation (COV) less than about 30%, less than about 25%, less than about 20%, less than about 15%, less than about 10% or less than about 5%, where the COV is defined as the standard deviation divided by the mean.

In one embodiment of the invention, a process of solvent shifting the aqueous nanoparticle dispersion to a less polar solvent composition by methods disclosed in commonly assigned U.S. Pat. No. 8,679,344 is employed. In a specific embodiment, the nanoparticle dispersion is passed through a diafiltration column along with the addition of an organic diluent. In a specific embodiment, the organic diluent comprises a surfactant, such as, for example, one or more alcohols or glycol ethers.

Without being bound by any theory, the proposed use of biocompatibly stabilized nanoceria for the prevention and/or treatment of inflammation and oxidative stress related events and diseases (e.g. reactive oxygen species (ROS) mediated diseases) is based in part upon a belief that cerium oxides may function as catalytic scavengers of free radicals. The existence of and facile inter-conversion of cerium in a mixture of $Ce^{3+}$ and $Ce^{4+}$ valence states may enable cerium oxides to reduce and/or oxidize free radicals to less harmful species in a catalytic or auto-regenerative manner. Redox reactions may occur on the surface of cerium oxide nanoparticles that neutralize tissue-damaging free radicals. For example, it is believed to be desirable to oxidize superoxide anion ($O_2^-$) to molecular oxygen, to oxidize peroxynitrite anion ($ONOO^-$) to physiologically benign species, and to reduce hydroxyl radical (.OH) to hydroxide anion. This may in turn enable a greatly reduced dosing regimen in comparison to, for example, sacrificial antioxidants currently available to treat oxidative stress related diseases and events.

In particular embodiments, administered nanoceria particles are taken into cells through cell membranes and reside in the cellular cytoplasm or in various cellular organelles, such as mitochondria and the nucleus. In other embodiments, the nanoceria particles reside in intravascular or interstitial spaces, wherein they may reduce oxidative stress and inflammation by reducing the buildup of hydrogen peroxide or by eliminating free radicals or reducing autoimmune responses. In a particular embodiment, the immune system invasion of the central nervous system resulting from breakdown of the blood-brain barrier (BBB) or blood-cerebrospinal fluid barrier (BCFB) or blood-ocular barrier (BOB) is modulated by nanoceria particles.

In another embodiment, the nanoceria particles are particles capable of crossing a mammalian blood brain barrier. In various embodiments, nanoceria particles cross a mammalian blood brain barrier and reside in brain parenchyma tissues as aggregates or agglomerates of a size less than about 100 nm, less than about 50 nm, less than about 20 nm, less than about 10 nm, less than about 5 nm. In various embodiments, nanoceria particles cross a mammalian blood brain barrier and reside in brain parenchyma tissues as independent, non-agglomerated nanoparticles of a size less than about 30 nm, less than about 5 nm, less than about 4 nm, less than about 3 nm, and less than about 2 nm.

In particular embodiments, a pharmaceutical composition comprises cerium-containing nanoparticles, such as nanoceria, and ethylenediaminedisuccinic acid; or, cerium-containing nanoparticles, such as nanoceria, prepared in the presence of ethylenediaminedisuccinic acid.

In particular embodiments, a pharmaceutical composition comprises cerium-containing nanoparticles, such as nanoceria, citric acid, and ethylenediaminedisuccinic acid; or, cerium-containing nanoparticles, such as nanoceria, prepared in the presence of citric acid and ethylenediaminedisuccinic acid.

In various embodiments, a pharmaceutical composition comprising cerium-containing nanoparticles, such as nanoceria, and ethylenediaminedisuccinic acid; or, cerium-containing nanoparticles, such as nanoceria, prepared in the presence of ethylenediaminedisuccinic acid; is administered to a human or a non-human subject, such as another mammal, including, but not limited to, a canine, a feline, a bovine, an equine, an ovine, a porcine or a rodent.

In various other embodiments, a pharmaceutical composition comprising cerium-containing nanoparticles, such as nanoceria, citric acid and ethylenediaminedisuccinic acid; or, cerium-containing nanoparticles, such as nanoceria, prepared in the presence of citric acid and ethylenediaminedisuccinic acid; is administered to a human or a non-human subject, such as another mammal, including, but not limited to, a canine, a feline, a bovine, an equine, an ovine, a porcine or a rodent.

In other embodiments, the subject of administration is an animal such as a bird, insect, reptile, amphibian, or any companion or agricultural animal. Alternatively, the subject of administration can be a bacterium, yeast, mold, fungus or another single celled organism. The subject of administration can also be a plant.

In another particular embodiment, a process of preventing (i.e. prophylactically treating) an oxidative stress related event, disease or cellular pathology, comprises administering prior to the onset of an event, disease or cellular pathology, an effective amount of a cerium-containing nanoparticle, such as nanoceria, and ethylenediaminedisuccinic acid, optionally further comprising citric acid; or, a cerium-containing nanoparticle, such as nanoceria, prepared in the presence of ethylenediaminedisuccinic acid, optionally further prepared in the presence of citric acid.

In another particular embodiment, a process of treating an oxidative stress related event, disease or cellular pathology, comprises administering after the onset of an event, disease or cellular pathology, an effective amount of a cerium-containing nanoparticle, such as nanoceria, and ethylenediaminedisuccinic acid, optionally further comprising citric acid; or, a cerium-containing nanoparticle, such as nanoceria, prepared in the presence of ethylenediaminedisuccinic acid, optionally further prepared in the presence of citric acid.

In various embodiments, a cerium-containing nanoparticle, such as nanoceria, of the invention is administered in vivo to a subject by topical, enteral or parenteral methods, including injections, infusions or implantations. More particularly, it is specifically contemplated to administer nanoceria particles of the invention by any of the following routes: auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intrabiliary, intrabronchial, intrabursal, intracardiac, intracartilaginous, intracaudal, intracavernous, intracavitary, intracerebral, intracisternal, intracorneal, intracornal-dental, intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmammary, transmucosal, transplacenta, transtracheal, transtympanic, ureteral, urethral, vaginal, and any other or unassigned route.

In various embodiments, oxidative stress related events and/or diseases specifically contemplated for prevention and/or treatment include, but are not limited to, Alzheimer's Disease, Parkinson's Disease, Huntington's Disease, amyotrophic lateral sclerosis (ALS), ataxia, Friedreich's ataxia, autism, obsessive-compulsive disorder, attention deficit hyperactivity disorder, migraine, ischemic stroke, traumatic brain injury, cancer, inflammation, autoimmune disorders, lupus, multiple sclerosis (MS), inflammatory bowel disease, Crohn's Disease, ulcerative colitis, stenosis, restenosis, atherosclerosis, metabolic syndrome, endothelial dysfunction, vasospasms, diabetes, aging, chronic fatigue, coronary heart disease, cardiac fibrosis, myocardial infarction, hypertension, angina, Prizmetal's angina, ischemia, angioplasty, hypoxia, Keshan disease, glucose-6-phosphate dehydrogenase deficiency, favism, ischemic reperfusion injury, rheumatoid and osteo-arthritis, asthma, chronic obstructive pulmonary disease (e.g. emphysema and bronchitis), allergies, acute respiratory distress syndrome, chronic kidney disease, renal graft, nephritis, ionizing radiation damage, sunburn, dermatitis, melanoma, psoriasis, macular degeneration, retinal degeneration, and cataractogenesis.

In various embodiments, oxidative stress related cellular pathologies specifically contemplated for prevention and/or treatment include, but are not limited to, mitochondrial dysfunction, lysosome and proteasome dysfunction, oxidation of nucleic acids (e.g. RNA and DNA), tyrosine nitration, loss of phosphorylation mediated signaling cascades, initiation of apoptosis, lipid peroxidation and destruction of membrane lipid environments.

In other embodiments, cerium-containing nanoparticles, such as nanoceria, of the invention are retained in or on the surface of a medical device or prosthesis, such as a cannula, catheter or stent, thereby, for example, reducing inflammation locally or systemically, over either a short or long time period.

In various embodiments, cerium-containing nanoparticles, such as nanoceria, of the invention are delivered in any suitable form known in the art, including, but not limited to, a suspension, gel, tablet, enteric coated tablet, loaded liposome, powder, suppository, infusible, lozenge, cream, lotion, salve, or inhalant.

In various embodiments, cerium-containing nanoparticles, such as nanoceria, of the invention are combined with other pharmaceutically acceptable substances, such as, but not limited to, water, salts, buffers, phosphate buffered saline (PBS), sugars, human or bovine serum albumen, lipids, drugs, colorants, flavorants, binders, gums, surfactants, fillers or any excipients known in the art.

In a particular embodiment, the vehicle comprising the cerium-containing nanoparticles, such as nanoceria, of the invention is sterilized prior to administration.

In other embodiments, a cell or cell culture is contacted with a cerium-containing nanoparticle, such as nanoceria, or particles of the invention. Contact may be practiced by exposing a cell or cell culture by in vitro or ex vivo methods, wherein the latter method comprises re-introducing the treated cell or cells into a subject, such as the subject from which the cell or cells were originally obtained. In various embodiments the cell is prokaryotic or eukaryotic in nature. In particular embodiments, the treated cells are used in the production of proteins used in the pharmaceutical industry, generally known as biologics, such as, but not limited to, antigens, antibodies and vaccines. In another embodiment, the treated cells are used in a fermentation process.

In an alternative end-use application, nanoceria particles of the invention are employed as a component of a chemical-mechanical polishing reagent for polishing substrates used, for example, in semiconductor devices, ceramics and optical elements. In particular embodiments, nanoceria particles of the invention are admixed into a magnetic fluid that changes in viscosity or other fluid properties upon application of a magnetic field. Some typical end uses for these magnetic fluids include shock absorbers, clutches, heat transfer devices and actuating modules, as described in U.S. Pat. No. 5,525,249. In a particular embodiment, it is specifically contemplated to employ nanoceria particles of the invention as an abrasive in a magnetorheological finishing (MRF) fluid used, for example, in a lens polishing operation, as described in U.S. Pat. No. 6,955,589. In a particular embodiment, dispersions containing about 20% by weight of the nanoceria particles of the invention are admixed into a MRF fluid. Some goals of adding an ultrafine abrasive such as the nanoceria of the invention to a MRF fluid are increased material removal rate, increased surface smoothness with fewer physical defects, improved chemical stability (e.g. reduced oxidation of magnetic particles) and improved physical stability (e.g. reduced settling) of the MRF fluid.

In a particular embodiment of the invention, a conjugate comprising (1) a nanoparticle comprising cerium and ethylenediaminedisuccinic acid, optionally further comprising citric acid; or, a cerium-containing nanoparticle prepared in the presence of ethylenediaminedisuccinic acid, optionally further prepared in the presence of citric acid; and (2) a biologically active agent, is provided. In particular embodiments, the biologically active agent comprises nucleic acid material, such as, for example, plasmid deoxyribonucleic acid, small interfering ribonucleic acid (siRNA), micro ribonucleic acid (miRNA), or an aptamer/riboswitch. In a particular embodiment the conjugate described supra is used as a cell transfection agent.

The invention is further illustrated by the following examples, which are not intended to limit the invention in any manner.

EXPERIMENTAL SECTION

Nanoparticle Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent.

Quantitative assessments of the particle size of the nanoparticle dispersions can be made by a number of techniques.

Dynamic light scattering (DLS) measurements were obtained using a Brookhaven 90Plus Particle Size Analyzer (Brookhaven Instruments Corp., Holtzville, N.Y., U.S.A.) equipped with a quartz cuvette. Samples were typically filtered through a 0.2 micron syringe filter prior to measurement to remove bacterial contaminants. Reported DLS sizes are the lognormal number weighted parameter. These hydrodynamic particle sizes are typically larger than sizes yielded by other techniques because the DLS technique includes contributions from adsorbed ions or molecules that constitute the solvation sphere of the particle.

Alternatively, particle size estimation by peak-width analysis of X-ray diffraction (XRD) spectra is done using the Scherrer method. Sample preparation for the XRD measurements is done as follows: liquid samples were mixed lightly, placed in a Telfon boat, allowed to dry under a heat lamp for several hours (until nearly dry), the resulting concentrated liquid was then placed onto a zero background quartz disk, allowed to dry under the heat lamp, and then dried in an oven at either room temperature or at about 80° C. for four hours under a dry nitrogen atmosphere. The coated disk was then analyzed by XRD using a nitrogen gas dry cell attachment. The XRD spectra were recorded on a Rigaku D2000 diffractometer equipped with copper rotating anode, diffraction beam graphite monochrometer tuned to copper K-alpha radiation, and a scintillation detector.

Alternatively, the size of the nanoparticles could be determined by direct analysis of transmission electron microscopy (TEM) images of the particles.

Catalase Activity Test

The ability of aqueous dispersions of cerium-containing nanoparticles to catalyze the elimination of hydrogen peroxide was determined using a Amplex® Red Catalase Assay Kit (A22180) purchased from Life Technologies, Inc., Carlsbad, Calif., USA. Catalase-like activity was measured on 60 μM concentration samples incubated for 1 hour, each sample was tested in triplicate and the results were averaged. Catalase unit activity was calculated based on a hydrogen peroxide standard curve.

Example 1

Preparation of Nanoceria with Citric Acid and EDTA

To a 0.8 L beaker at room temperature, 500 grams of distilled water, 10 grams of cerium nitrate hexahydrate, 2.4 grams of citric acid and 4.3 grams of ethylenediaminetetraacetic acid disodium salt (EDTA) were added, mixed and dissolved. Then concentrated ammonium hydroxide (28-30%) was added until the solution pH was 8.5. The reaction mixture was heated to 80° C. Subsequently, 4.8 ml of hydrogen peroxide (50%) was added, and the reaction held at 80° C. for about 1 hour, resulting in a clear yellow/orange suspension. The suspension was cooled to room temperature, and then washed by diafiltration to remove excess salts to an ionic conductivity of less than about 10 mS/cm. The pH of the final product dispersion was about 7.2.

The molar ratios among cerous ion/citric acid/EDTA that were added to the reaction mixture were 1.0/0.5/0.5, respectively.

The final product dispersion was a clear light orange colored liquid that displayed a high degree of Tyndall scattering when illuminated with a low intensity LASER beam, a test for well-dispersed colloidal particles. Particle size analysis by dynamic light scattering indicated a hydrodynamic diameter of 3.1 nm. The final reaction product dispersion was observed to be stable (i.e. well-dispersed) for several months. Phase identification by powder XRD analysis indicated the presence of a phase iso-structural with $CeO_2$ (PDF #34-394). The average crystallite size for the nanoceria particles was determined to be 2.4 nanometers from analysis of the (220) powder XRD peak width using the Scherrer method.

Example 2

Preparation of Nanoceria with EDDS

Aqueous reaction procedures similar to those used in Example 1 were repeated, except that the addition of citric acid was eliminated, and that 23.5 grams of a 35% solution of ethylenediaminedisuccinic acid trisodium salt (EDDS) was added instead of ethylenediaminetetraacetic acid disodium salt (EDTA). In this way, equimolar amounts of cerous ion and EDDS were added.

The final product dispersion was a mostly clear, dark red/orange colored liquid that displayed a high degree of Tyndall scattering when illuminated with a low intensity LASER beam. Particle size analysis by dynamic light scattering indicated a hydrodynamic diameter of 29.5 nm with a polydispersity of 0.145.

Example 3

Preparation of Nanoceria with Citric Acid and EDDS

Aqueous reaction procedures similar to those used in Example 1 were repeated, except that an equimolar amount of ethylenediaminedisuccinic acid trisodium salt (EDDS) was used instead of ethylenediaminetetraacetic acid disodium salt (EDTA).

The molar ratios among cerous ion, citric acid and EDDS were 1.0/0.5/0.5, respectively.

The final reaction product was a clear light orange colored liquid that displayed a high degree of Tyndall scattering when illuminated with a low intensity LASER beam, a test for well-dispersed colloidal particles. Particle size analysis by dynamic light scattering indicated a hydrodynamic diameter of 2.7 nm with a polydispersity of 0.147.

The final reaction product dispersion was observed to be stable (i.e. well-dispersed) for at least 18 months.

Phase identification by powder XRD analysis indicated the presence of a phase iso-structural with $CeO_2$ (PDF #34-394). The average crystallite size for the nanoceria particles was determined to be 2.1 nanometers from analysis of the (220) powder XRD peak width using the Scherrer method.

Catalase-like activity was evaluated for each of the nanoparticle product dispersions prepared in Examples 1-3 using the Catalase Activity Test described above.

| Example | Stabilizers | Catalase Activity (mU/ml) |
|---|---|---|
| 1 | CA/EDTA | 630 |
| 2 | EDDS | 350 |
| 3 | CA/EDDS | 1010 |

"Results are given in the table above".

Examination of the results shown in the table above indicates that both of the nanoparticle dispersions prepared with EDDS have substantial catalase-like activity. In particular, the nanoparticle dispersion prepared in Example 3 with citric acid and EDDS displayed the greatest amount of catalase-like activity.

While the invention has been described by reference to various specific embodiments, it should be understood that numerous changes may be made within the spirit and scope of the inventive concepts described. Accordingly, it is intended that the invention not be limited to the described embodiments, but will have full scope defined by claims language.

The invention claimed is:

1. A method of making a dispersion of nanoparticles, comprising:

a. forming a reaction mixture comprising cerous ion, ethylenediaminedisuccinic acid, citric acid, hydroxide ion, and water;
b. heating the reaction mixture;
c. adding an oxidant to the reaction mixture; and
d. forming in the reaction mixture a dispersion of cerium oxide nanoparticles.

2. The method of claim 1, wherein the reaction mixture is heated at a temperature in the range of about 30° C. to about 100° C.

3. The method of claim 1, wherein said oxidant comprises hydrogen peroxide.

4. The method of claim 1, wherein said cerium oxide nanoparticles are substantially non-agglomerated.

5. The method of claim 1, wherein said cerium oxide nanoparticles have a hydrodynamic diameter less than about 30 nanometers.

6. The method of claim 1, wherein said cerium oxide nanoparticles have a hydrodynamic diameter less than about 5 nanometers.

* * * * *